(12) United States Patent
Goto et al.

(10) Patent No.: US 6,862,089 B2
(45) Date of Patent: Mar. 1, 2005

(54) METHODS FOR MANAGING EXAMINATION OF FOREIGN MATTERS IN THROUGH HOLES

(75) Inventors: Noboru Goto, Yamagata-ken (JP); Hideshi Tsutsui, Yamagata-ken (JP); Mikio Saito, Yamagata-ken (JP)

(73) Assignee: Seiko Epson Corporation (JP)

( * ) Notice: Subject to any disclaimer, the term of this patent is extended or adjusted under 35 U.S.C. 154(b) by 307 days.

(21) Appl. No.: 09/999,764

(22) Filed: Oct. 24, 2001

(65) Prior Publication Data

US 2002/0109837 A1 Aug. 15, 2002

(51) Int. Cl.$^7$ ............................................. G01N 21/88
(52) U.S. Cl. ................... 356/237.6; 356/237.2
(58) Field of Search ...................... 356/237.2, 237.3, 356/237.4, 237.5, 326, 445, 630; 250/559.4, 252

(56) References Cited

U.S. PATENT DOCUMENTS

| | | | | |
|---|---|---|---|---|
| 3,873,211 A | * | 3/1975 | Watson | 356/156 |
| 4,145,714 A | * | 3/1979 | Nakajima et al. | 356/372 |
| 5,808,734 A | * | 9/1998 | Kolari | 356/237 |
| 5,923,430 A | * | 7/1999 | Worster et al. | 356/394 |
| 5,963,314 A | * | 10/1999 | Worster et al. | 356/237.2 |

FOREIGN PATENT DOCUMENTS

| | | |
|---|---|---|
| JP | 5-215696 | 8/1993 |
| JP | 11-304419 | 11/1999 |
| JP | 2000-292365 | 10/2000 |

* cited by examiner

*Primary Examiner*—Zandra V. Smith
(74) *Attorney, Agent, or Firm*—Harness, Dickey & Pierce, P.L.C.

(57) ABSTRACT

A method for managing an apparatus for examination of foreign matters in through holes is provided which can readily judge the presence or absence of a change in the examination conditions in the apparatus for examining foreign matters in through holes, and efficiently conduct a management of the apparatus. When light passing through a minute through hole formed in a workpiece are taken by a camera as image data, and the presence or absence of a foreign matter in the through hole is examined based on an area of passing light that corresponds to the through hole examined, a reference workpiece is selected, an operation to measure an area of light passing through the through holes of the reference workpiece is periodically performed and measured values are stored in a data base, a change state in the area of passing light obtained from the data base is compared with pre-set management standard values, and an adjustment timing and an adjustment object in the examination apparatus are selected to perform an examination adjustment.

5 Claims, 7 Drawing Sheets

| Position of Hole | Management Standard Value | | Measured Value |
|---|---|---|---|
| | Lower Limit | Upper Limit | |
| 1 | 312 | 412 | 378 |
| 2 | 322 | 422 | 386 |
| 3 | 315 | 415 | 378 |
| 4 | 318 | 418 | 379 |
| . | . | . | . |
| . | . | . | . |
| N | 330 | 430 | 382 |

Fig. 8
PRIOR ART

Work With A Plurality Of Minute Holes

Image Taking
(Minute Hole / Hole)

METHODS FOR MANAGING EXAMINATION OF FOREIGN MATTERS IN THROUGH HOLES

TECHNICAL FIELD OF THE INVENTION

The present invention relates to a method for managing examination of foreign matters in through holes, and more particularly to a method that is suitable to the management of examination of the presence or absence of foreign matters in through holes having a minute diameter.

BACKGROUND OF THE INVENTION

Figure 8:
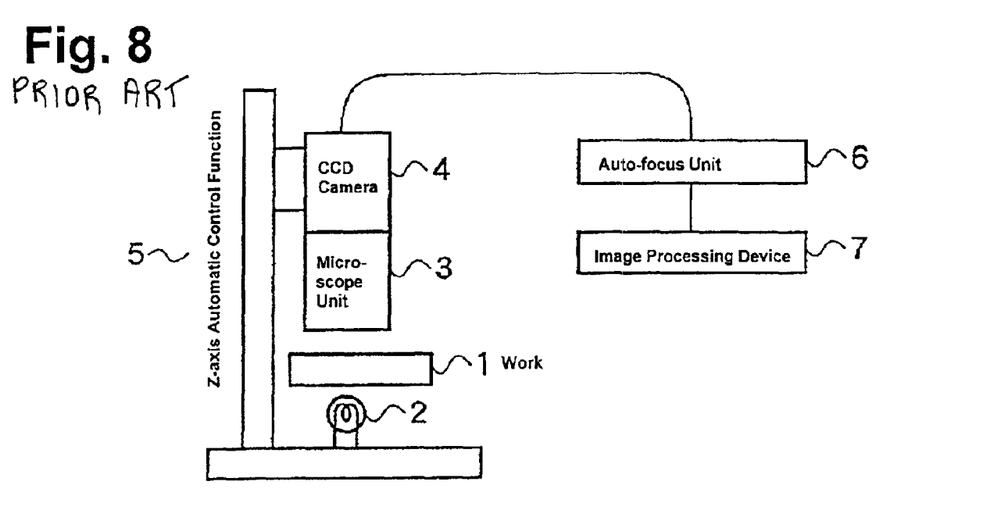
FIG. 8 is an illustration to describe a conventional foreign matter examination apparatus.

First, a conventional apparatus for examining foreign matters in through holes is described with reference to FIG. 8. Generally, examinations are conducted for through holes having diameters of several tens to several hundred micrometers to check if they are perforated in a correct number, if the sizes of the through holes are uniform, if foreign matters are present inside thereof, and the like. Normally, optical methods are used to perform the examinations described above. For example, an examination surface of a workpiece in which through holes are formed is photographed by a CCD camera through a microscope, and the result is compared with a reference value by an image processing apparatus to make an acceptance/non-acceptance judgment. In this conventional example, an auto-focus unit, a microscope, or an electron beam is required in addition to the image processing apparatus, and the examination is conducted for each of the through holes, and with an enlarged image at a high magnification.

Figure 2:
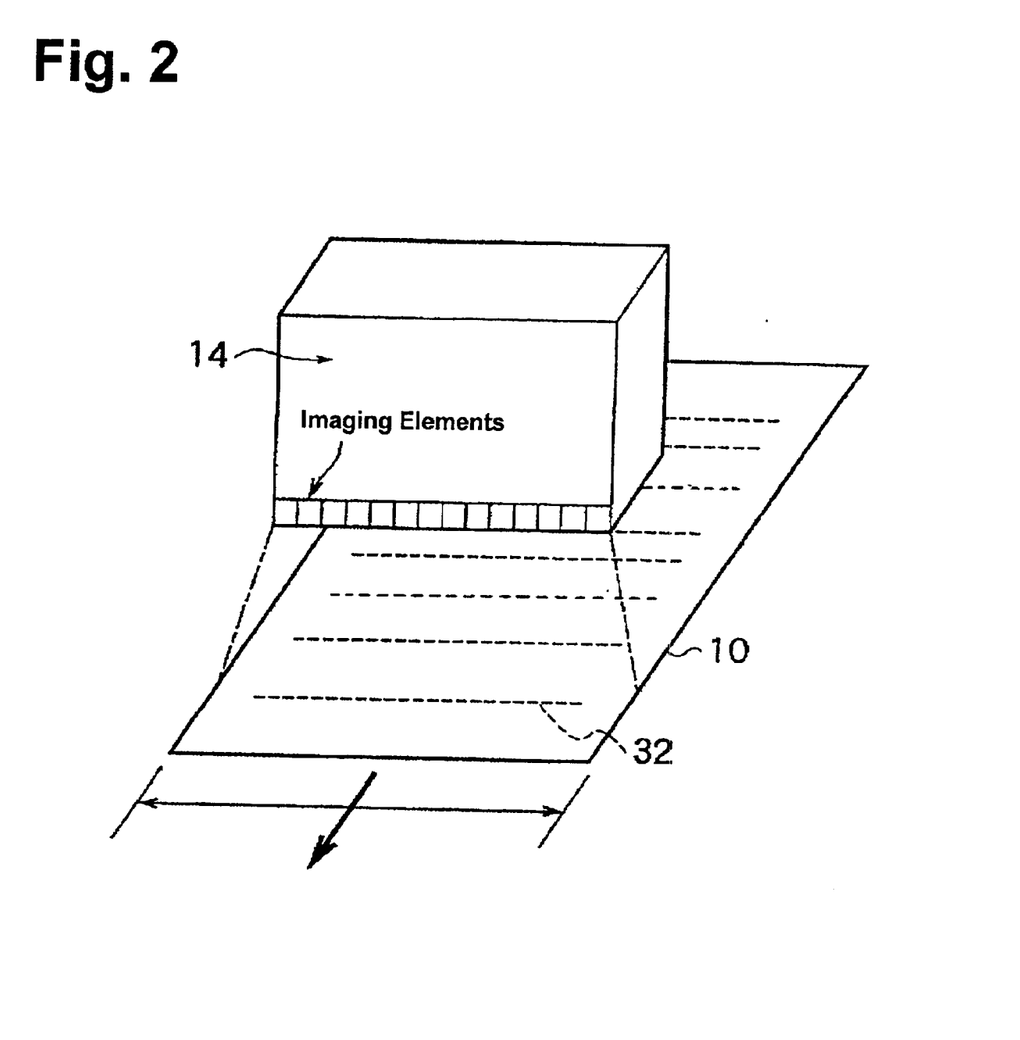
FIG. 2 is an illustration to describe a line sensor camera and a workpiece.

The examination apparatus of the type described above generally has a structure shown in FIG. 8, in which a workpiece 1 having through holes formed therein is disposed at a predetermined position, a light source 2 is disposed on the side of a lower surface of the work, and an image taking device with an integral unit of a microscope unit 3 and a CCD camera 4 is disposed on the side of an upper surface of the work piece 1. The image-taking device can be elevated up and down by a z-axis automatic control mechanism 5. Also, the CCD camera 4 is connected to an image processing apparatus 7 through an auto-focus unit 6. By using this examination apparatus, the workpiece 1 having a plurality of through holes shown in FIG. 2 is photographed, in which a through hole acceptance/non-acceptance judgment is conducted based on an image taken in the unit of each of the through holes 8. For example, when a foreign matter is present in the through hole 8, the amount of passing light is reduced, and an area of the measured pixel becomes smaller. The through hole 8 having a pixel area that is smaller than a predetermined threshold value is judged as being defective.

In the apparatus for examining foreign matters in through holes described above, the diameter of each through hole is very small, and a highly magnified image is taken. As a result, a slight change in the examination conditions such as the position of the work, the camera or the like greatly affects the area value of passing light, and therefore the detection of foreign matters may not be effectively conducted. As such the examination conditions of the examination apparatus need to be well managed. Accordingly, the presence or absence of such a change in the examination conditions of the examination apparatus is judged by individually examining each of the parts of the apparatus and its examination condition.

However, in the apparatus for examining foreign matters in through holes described above, many parts of the apparatus and their examination conditions affect the size of an area value of passing light to be measured. For example, the positions and performances of the workpiece 1, the light source 2, the microscope unit 3, the CCD camera 4 and the z-axis adjusting mechanism 5 shown in FIG. 8 are all contributing factors to the size of the area value of passing light. Accordingly, substantial time and costs are required to individually examine all of the parts and their conditions, and the presence or absence of a change in the examination conditions cannot be confirmed in many occasions. This is inconvenient because the apparatus management cannot be sufficiently conducted.

In view of the inconvenience of the conventional art, it is an object of the present invention to provide a method for managing an examination of foreign matters in through holes, which can readily judge the presence or absence of a change in the examination conditions in an apparatus for examining foreign matters in through holes, and efficiently conduct the examination management.

SUMMARY OF THE INVENTION

To achieve the above object, a method for managing an apparatus for examining foreign matters in through holes is provided. In accordance with the present invention, when light passing through a minute through hole formed in a work is taken by a camera as image data, and the presence or absence of a foreign matter in the through hole is examined based on an area of passing light that corresponds to the through hole examined, the method selects a reference work, periodically performs an operation to measure an area of light passing through the through holes of the reference work and stores measured values in a data base. The method compares a change state in the area of passing light obtained from the data base with pre-set management standard values, and selects an adjustment timing and an adjustment object in the examination apparatus to perform an examination adjustment. As a result, the presence or absence of a change in the examination conditions of the examination apparatus can be readily judged, and an efficient management of examination of foreign matters in through holes can be realized.

Also, a plurality of columns of through holes designated at a plurality of locations on the workpiece may preferably be set as through holes to be measured in the reference work, and the designated columns of through holes may preferably be measured periodically.

Furthermore, the management standard values may preferably be set for each of the through holes, within a range between an upper limit allowable value and a lower limit allowable value centered at a reference set value being set as an initial measurement value for each of the through holes, and an adjustment timing of the examination conditions and an adjustment object may preferably be selected based on a comparison/judgment with the management standard value for each of the through holes to perform an examination adjustment.

DETAILED DESCRIPTION OF THE PREFERRED EMBODIMENTS OF THE INVENTION

An embodiment of the present invention, in which a method for managing examination of foreign matters in through holes in accordance with the present invention is applied to an apparatus for examining foreign matters in through holes of a product having a plurality of through holes having a minute diameter, is described in detail with reference to the accompanying drawings.

FIG. 2 shows an example of a product (workpiece). A workpiece 10 has a plurality of through holes 32, in other words, pierced holes. In the case of a product having through holes of a minute diameter, there are cases in which adhesion of minute foreign matters invisible to naked eyes to through holes may lead to a lowered performance of the product. Accordingly, it is necessary to examine whether or not foreign matters are adhered to through holes of the product.

Figure 3:
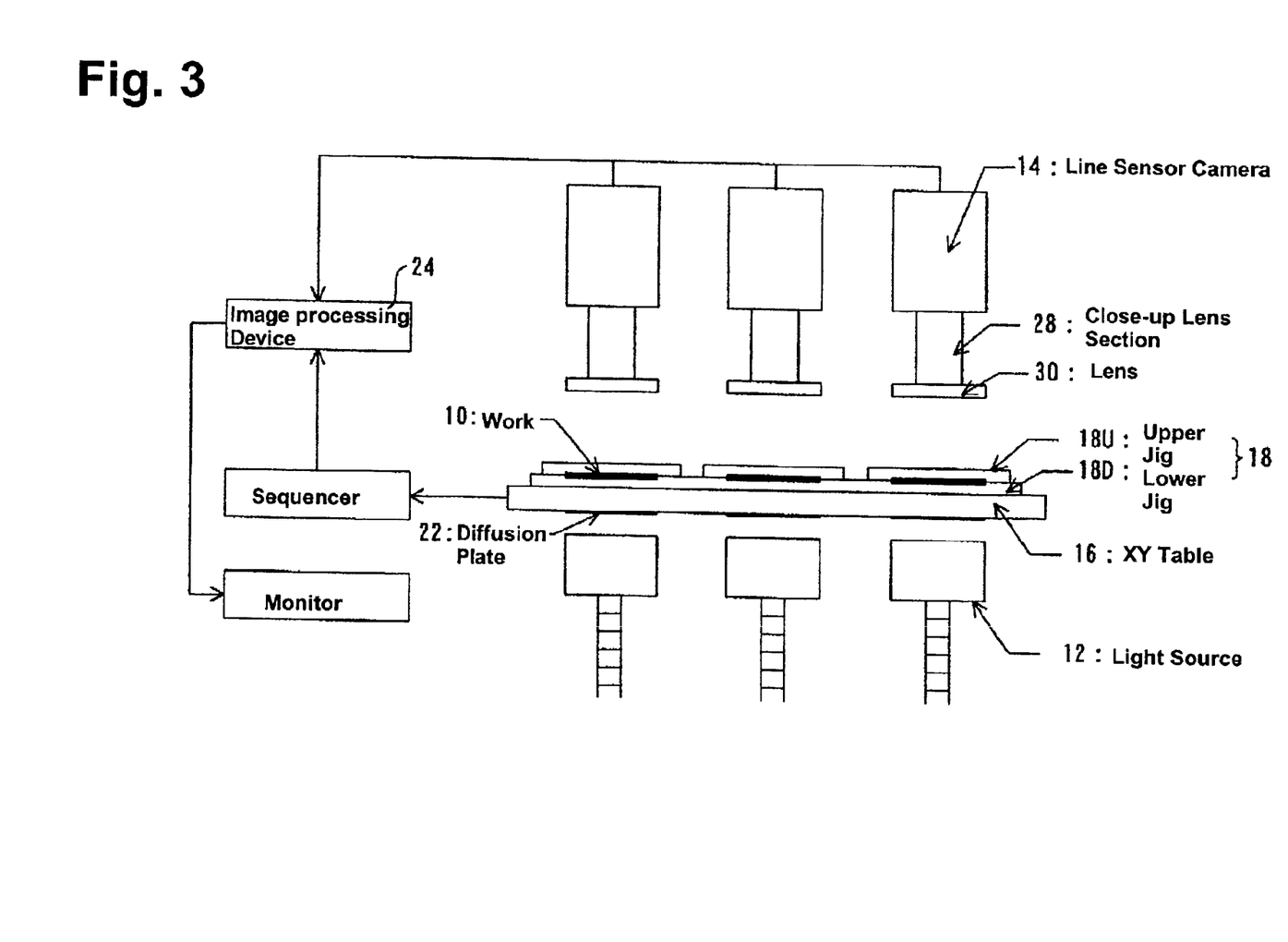
FIG. 3 shows a block diagram of an apparatus for examining foreign matters in through holes.
Figure 4:
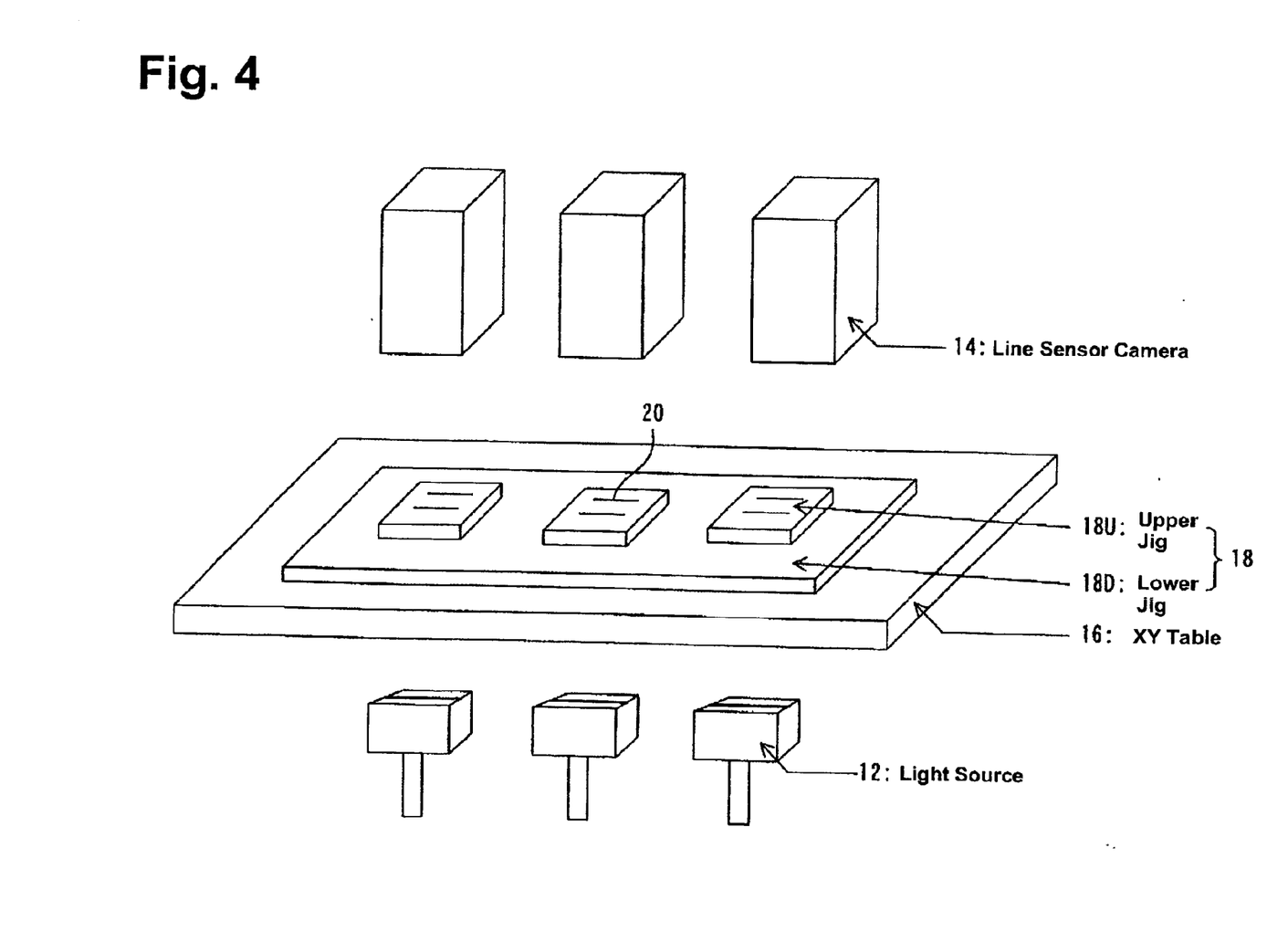
FIG. 4 is an illustration to describe an apparatus for examining foreign matters in through holes.

FIG. 3 shows a structure of an examination apparatus that is used in a process for examining foreign matters in through holes. The examination apparatus has a structure in which a light source 12 is disposed on the side of a lower surface of a plate-shaped workpiece 10 having a plurality of through holes arranged in columns to irradiate light from behind toward the through holes. On the other hand, a line sensor camera 14 having a plurality of CCD elements arranged in a column is disposed on the side of an upper surface of the workpiece 10 wherein the light passing through the through holes is photographed by the camera 14 (see FIG. 2). Accordingly, light is irradiated on the workpiece 10 by the light source 12 disposed on one plane side of the workpiece 10, and photographed by the line sensor camera 14 that is disposed on the opposite side of the light source 12 with the workpiece 10 interposed between them. Then, the line sensor camera 14 and the light source 12 are moved in a plane direction with respect to the workpiece 10, and a plane image of passing light is photographed to thereby take the image. In the present embodiment, the workpiece 10 is mounted on an XY table 16 and moved in a direction orthogonal to the columns of pixels to perform scanning (see FIG. 4).

Then, the image data is input in an image processing device 24 whereby a detection of foreign matter is conducted by using the characteristic in which, when a foreign matter is present in a through hole, an area value of the through hole becomes smaller as a result of the foreign matter blocking the light. It is noted that, since the example shown in FIG. 3 examines three workpieces 10 at once, the light sources 12 and the sensor cameras 14 are provided in three pairs.

In order to dispose the works 10 at predetermined locations on the XY table 16, a fixing jig 18 is used to clamp the workpieces 10. This is formed from a lower jig 18D and an upper jig 18U, and an appropriate fixing device is used to position and fix the jig 18 at a predetermined position on the table. The jig 18 is provided with slits 20 corresponding to the columns of through holes of the workpiece 10 such that the line sensor camera 14 takes in light passing through the slits 20. Also, the light source 12 disposed below the XY table 16 is structured to achieve a line illumination (see FIG. 4). A diffusion plate 22 is mounted on the under surface section of the table to diffuse variations of the intensity of light from the light source 12 to thereby irradiate uniform light on the columns of through holes.

Figure 1:
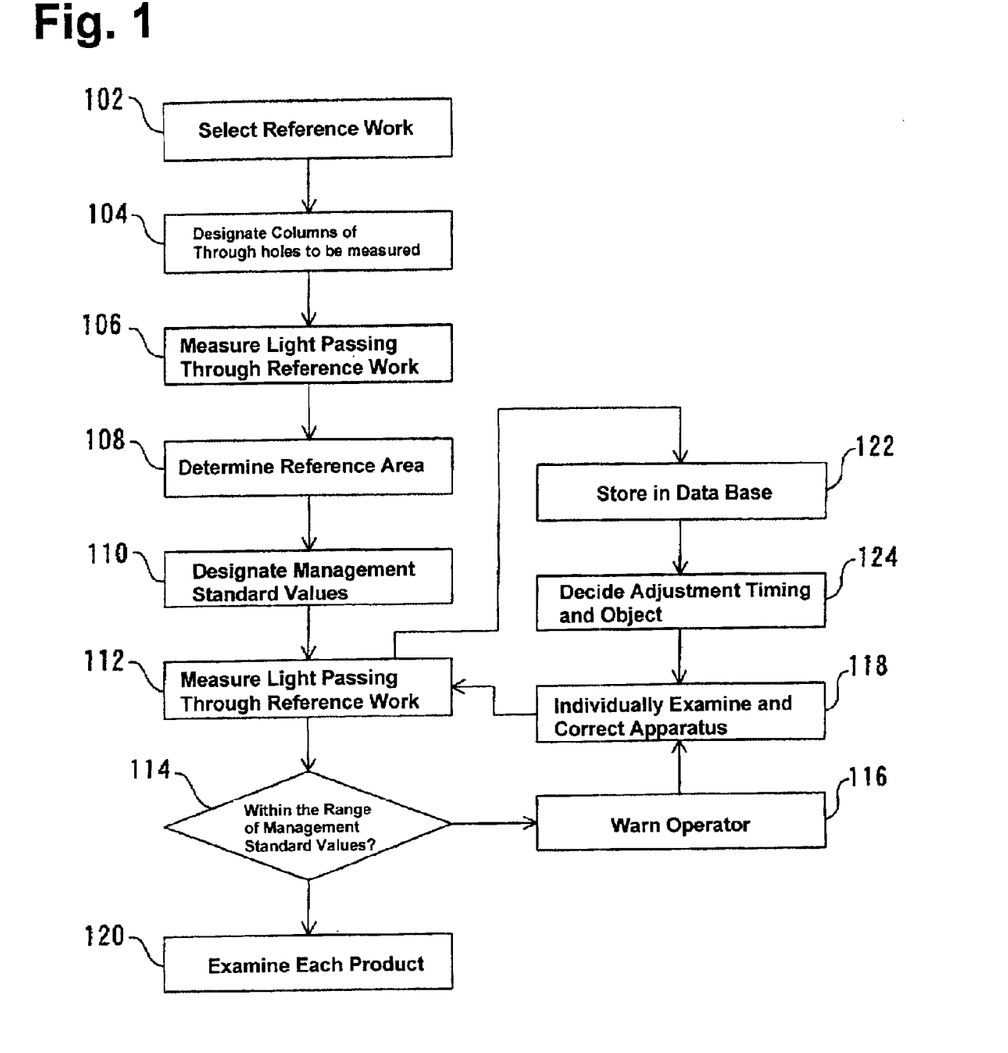
FIG. 1 shows a block diagram of a method for managing an apparatus for examining foreign matters in through holes in accordance with the present invention.

FIG. 1 shows a block diagram of a method for examining foreign matters in through holes using a reference work, which is a characteristic structure of the present invention. First, reference set values and a method for determining management standard values are described.

First, a reference workpiece is selected (step 102). It is necessary to select a reference workpiece in which no foreign matter is adhered to its through holes. Accordingly, a method in which a microscope is used to visually inspect the through holes may be employed, and a selection should be made upon confirmation that no foreign matter is present. It is noted that, if the measurement of each section of the reference workpiece changes after the reference set values are measured, or foreign matter adheres to the through holes, an area value of passing light changes, and the apparatus cannot be managed by the reference workpiece thereafter. Accordingly, the reference workpiece should be placed in a case to control its temperature and humidity in a manner to avoid an application of an undesired force, and stored under a strict environment where minute foreign matters such as dusts are removed.

Next, columns of through holes to be measured are designated (step 104). The measurement of an area of passing light in the present embodiment is conducted to manage the examination apparatus, and not for examination of foreign matters in through holes of a reference workpiece. Therefore it does not need to be conducted for all of the through holes of the work.

Figure 5:
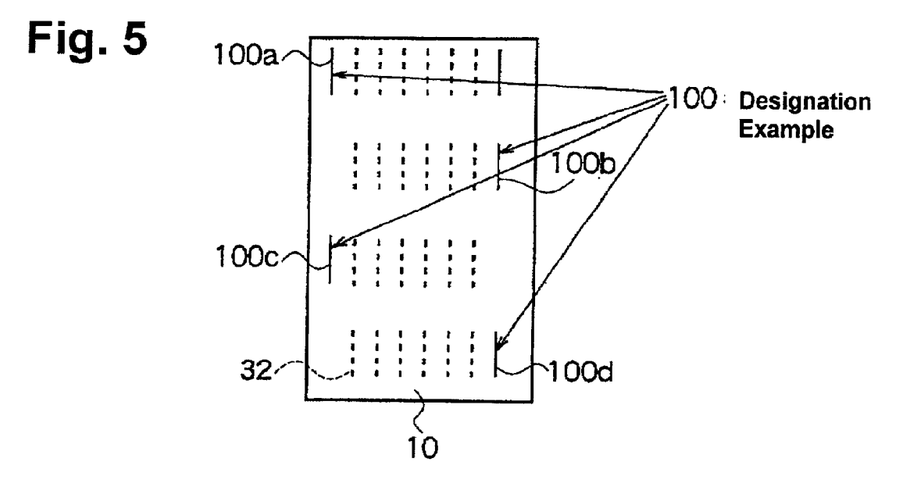
FIG. 5 shows an example of designation of columns of through holes to measure a passing light area.

Accordingly, certain columns of through holes for measurement of an area of passing light are initially designated, and thereafter all measurements of passing light are conducted only for the designated columns of through holes. FIG. 5 shows an example of designating columns of through holes. In the example shown in FIG. 5, a column 100a on the left end in the first row, a column 100b on the right end in the second row, a column 100c on the left end in the third row, and a column 100d on the right end in the second row are designated. In designating the columns of through holes, any columns may be designated without being limited to the example shown in FIG. 5. However, if the designated columns are concentrated in one area of the work, there may be occasions in which changes in the examination conditions of the examination apparatus cannot be detected. For example, even when the position of the light source is shifted in a horizontal direction, if it is shifted in the direction of the designated column, no change may be detected in the area value of passing light. Accordingly, columns of through holes are designated to be uniformly located from each section of the workpiece (for example, at both of the end sections and the central section in each row) like the one shown in the example of FIG. 5.

In this manner, by measuring an area of passing light of not the entire through holes but only a part of the through holes that are initially designated, the examination time is shortened, and an efficient apparatus management is realized. Also, by designating through holes uniformly from each section of the workpiece, a change in the examination conditions cannot be missed.

Next, an area of passing light is measured for the designated columns of through holes on the reference workpiece (step 106), and a first measurement result is set as a reference set value for each of the through holes (step 108). Since the reference set value defines a reference for judgment of a change in the examination conditions of the examination apparatus, the area of passing light is measured upon individually inspecting each section of the apparatus and its examination condition as described below.

Figure 6:
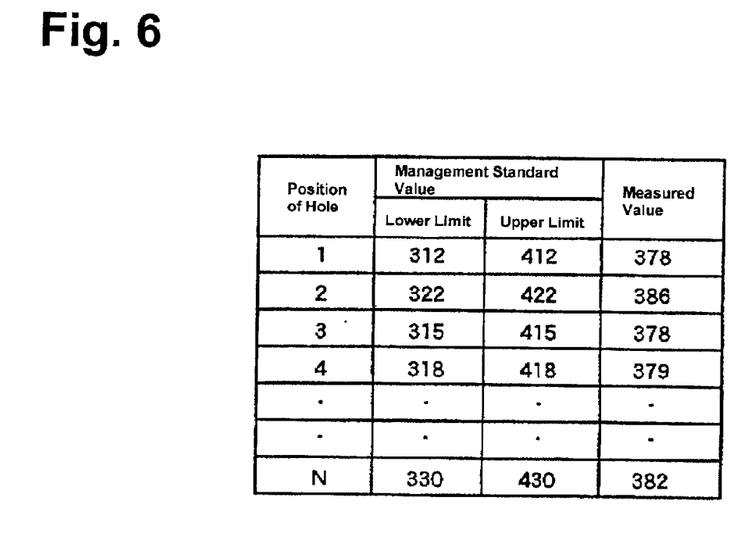
FIG. 6 shows an example of management standard values for each through hole in a column of through holes.

Next, management standard values centered on the reference set value are determined (step 110). The management standard values are area values of passing light that correspond to an upper limit value and a lower limit value of acceptable changes in the examination conditions of the examination apparatus, and are set with upper and lower margins centered on the reference set value for each through hole. The management standard values are determined in view of the manner of variations in the realistic examination conditions and the size of a foreign matter to be detected. FIG. 6 shows an example of management standard values for the respective through holes included in a designated column of through holes. In the example shown in FIG. 6, a margin of an area value of 50 units centered on the reference set value is given above and below for each of the through holes to thereby set upper limit values and lower limit values of the management standard values.

Secondly, a method for determining the presence or absence of a change in the examination conditions of the examination apparatus is described. The area of passing light is measured for the reference workpiece at predetermined intervals (step 112), for example everyday before workpiece examinations are started. Next, a determination is made as to whether the area value of passing light is within the range of the management standard values centered at the reference set value (step 114). In the example shown in FIG. 6, the measured value of each of the through holes is within the range of the management standard values.

When the area value of passing light is not within the range of the management standard values, the operator is warned (step 116), each section of the apparatus and its examination condition are individually investigated and corrected (step 118). Sections of the examination apparatus that may affect the area value of passing light include the light source 12, the diffusion plate 22, the XY table 16, the jig 18 and the line sensor camera 14. Examination conditions that may affect the area value of passing light for each section include positions in the horizontal and vertical directions, the orientation, the light intensity, and the color of light with respect to the light source 12; the position in the vertical direction and discoloration with respect to the diffusion plate 22; the position in the vertical direction and the parallel degree with respect to the XY table 16 and the jig 18; and the directions in the horizontal and vertical directions, the orientation, the focal point position, changes in the performance of the lens and CCD with respect to the line sensor camera 14. After these aspects are examined and corrected, the area of the passing light of the reference workpiece is measured again (step 112) to determine whether it is corrected to be within the scope of the management standard values (step 114).

On the other hand, when the area value of passing light is within the range of the management standard values, examination of foreign matters in through holes is started for each of the products (step 120).

Figure 7:
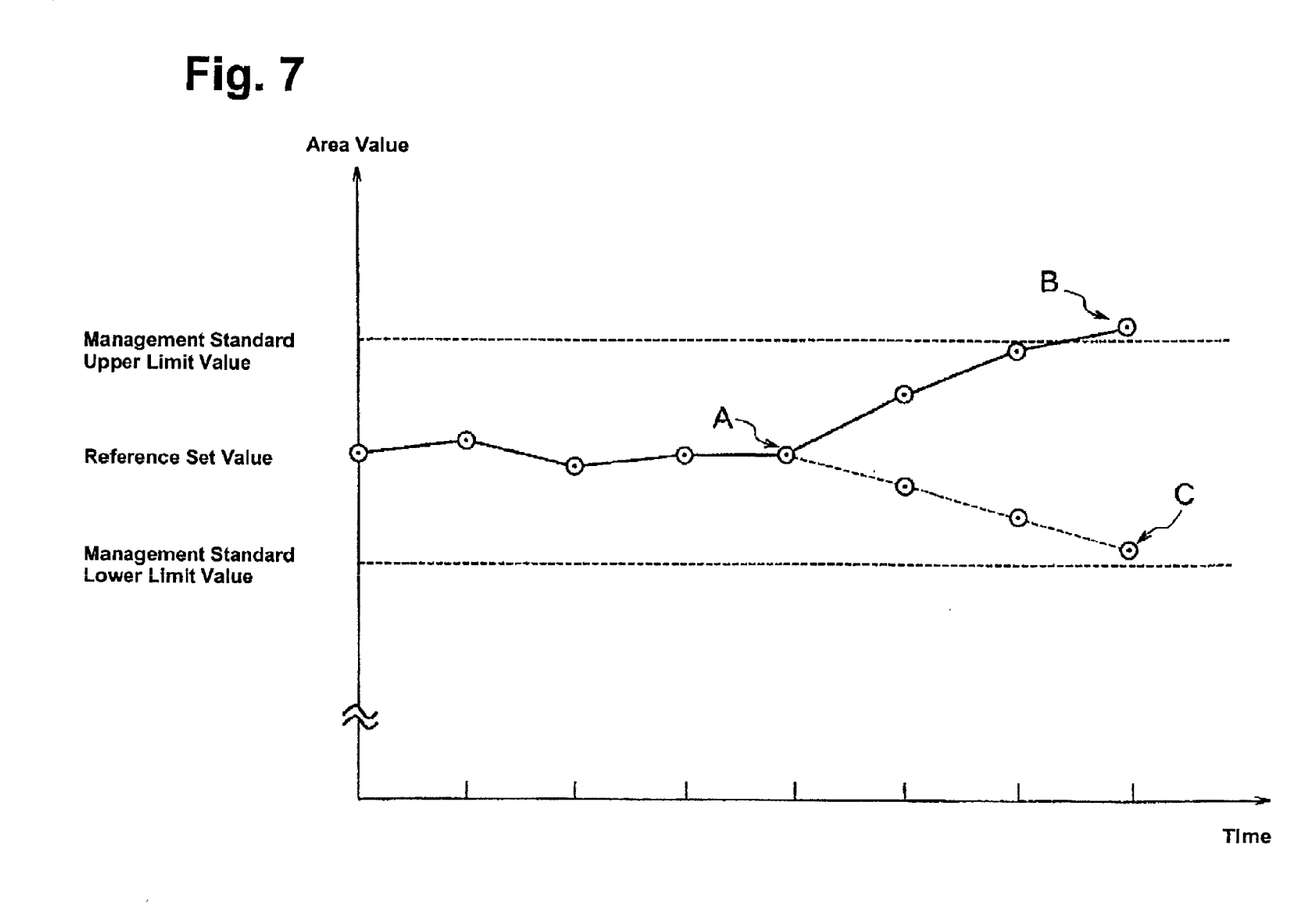
FIG. 7 shows an example of a graph that indicates changes in each measurement of passing light area values for a through hole.

Measured results of the areas of passing light obtained at predetermined intervals in step 112 are stored in a database, and used for tendency management of the examination apparatus (step 122). More particularly, a graph shown in FIG. 7 is formed. FIG. 7 shows an example of a graph that indicates how the area value of passing light for a through hole changes at each measurement. According to the example shown in FIG. 7, the area value of passing light starts increasing at point A, and exceeds the management standard value at point B. Based on the graph, a consideration can be made as to when the change in the examination conditions started, what the possible cause was corresponding to that period, and the like. Also, the area value of passing light continually reduces from point A toward point C in FIG. 7. In this case, although the value is still within the range of the management standard values at point C, it is expected to exceed the management standard values with the passage of time. Accordingly, a decision of adjustment time, at which the examination conditions of the examination apparatus should be corrected, can be made. Furthermore, this graph may be formed for each of the through holes. When the through holes in which the area values of passing light change are concentrated in a certain area, each section of the examination apparatus corresponding to that section (for example, the light source) is considered to be shifted in its position, such that an object to be adjusted and its direction to be corrected can be decided (step 124). In addition, by forming such graphs only for the through holes that are uniformly designated in advance on the workpiece, the time required for the examination and the time for forming the graphs can be shortened, and changes that convergently occur in a certain portion of the workpiece should not be missed.

Then the examination timings and the determination results of the examination objects may be reflected on the examination and correction of the examination conditions in step 118 shown in FIG. 1, such that focused examination and correction can be conducted, and the apparatus management can be efficiently conducted.

By the method described above, the presence or absence of a change in the examination conditions of the examination apparatus can be appreciated based on a change in the area value of passing light. Also, since the measurements to be conducted at predetermined intervals are conducted in the same manner as those conducted for ordinary products, and only the designated columns of through holes are measured, the presence or absence of a change in the examination conditions of the examination apparatus can be readily determined. Furthermore, each section of the apparatus and its examination condition can be examined individually only after it is confirmed that there is a change in the examination conditions. Accordingly, the examination efficiency is substantially improved, and the apparatus management can be efficiently conducted. Furthermore, by measuring an area of passing light of not the entire through holes but only a part of the through holes that are designated in advance, the time for examination can be shortened, and an efficient apparatus management can be realized. In addition, by storing area values of passing light obtained at predetermined time intervals in step 112 in a database, the tendency of changes in the examination conditions of the examination apparatus can be understood, and they can be incorporated into the correction of the examination conditions. Accordingly, a specially efficient and effective apparatus management can be realized.

What is claimed is:

1. A method for managing an examination apparatus which passes light through a through hole formed in a workpiece, captures the light with a camera as image data, and a presence or absence of foreign matter in said through hole is examined based on an area of passing light that corresponds to said through hole examined, the method comprising:

selecting a reference workpiece;

periodically measuring an area of light passing through select through holes of said reference workpiece and storing measured values in a data base;

comparing a change state in said area of passing light obtained from said data base with pre-set management standard values;

selecting an adjustment timing and an adjustment object in said examination apparatus for performing an examination adjustment;

designating a plurality of columns of through holes at a plurality of locations on the workpiece as said select through holes to be measured in the reference workpiece, and periodically measuring the select through holes.

2. A method for managing an examination apparatus which passes light through a through hole formed in a workpiece, captures the light with a camera as image data, and a presence or absence of foreign matter in said through hole is examined based on an area of passing light that corresponds to said through hole examined, the method comprising:

selecting a reference workpiece;

periodically measuring an area of light passing through select through holes of said reference workpiece and storing measured values in a data base;

comparing a change state in said area of passing light obtained from said data base with pre-set management standard values; and selecting an adjustment timing and an adjustment object in said examination apparatus for performing an examination adjustment;

wherein said management standard values are set for each of the through holes of the reference workpiece, within a range between an upper limit allowable value and a lower limit allowable value centered at a reference set value which is set as an initial measurement value for each of the through holes, and said adjustment timing of the examination conditions and said adjustment object are selected based on a comparison with said management standard values for each of the through holes.

3. A method for adjusting an examination apparatus which examines a workpiece by passing light through a through hole in said workpiece, capturing the light with a camera as image data, and examining an area of the light to determine whether foreign matter is present in said through hole, said method comprising:

selecting a reference workpiece;

setting an initial measurement value for each through hole formed in said reference workpiece according to an area of light passing through each through hole;

periodically taking measured values of an area of light passing through select through holes of said reference workpiece with said examination apparatus;

comparing said measured values with said initial measurement values;

adjusting said examination apparatus if said measured values differ from said initial measurement values by more than a pre-selected amount; and tracking a trend of differences between said measured values and said initial measurement values.

4. The method of claim 3 wherein said step of adjusting said examination apparatus further comprises adjusting a component of said examination apparatus based on said trend.

5. The method of claim 3 wherein said step of adjusting said examination apparatus further comprises adjusting said examination apparatus at a time based on said trend.

* * * * *